US012806322B2

(12) United States Patent
Yuds et al.

(10) Patent No.: US 12,806,322 B2
(45) Date of Patent: Nov. 24, 2026

(54) MEDICAL DEVICE DRAIN SYSTEM FOR MANAGING AND MONITORING WASTE MEDICAL FLUID

(71) Applicants: Fresenius Medical Care Holdings, Inc., Waltham, MA (US); FRESENIUS MEDICAL CARE DEUTSCHLAND GMBH, Bad Homburg (DE)

(72) Inventors: David Yuds, Hudson, NH (US); Lena Mandelka, Hochheim (DE); Shu Yun Wang, Malden, MA (US)

(73) Assignees: Fresenius Medical Care Holdings, Inc., Waltham, MA (US); FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 360 days.

(21) Appl. No.: 18/434,242

(22) Filed: Feb. 6, 2024

(65) Prior Publication Data

US 2025/0249160 A1 Aug. 7, 2025

(51) Int. Cl.
*A61M 1/28* (2006.01)
*A61M 1/00* (2006.01)
(Continued)

(52) U.S. Cl.
CPC ............ *A61M 1/28* (2013.01); *A61M 1/1692* (2013.01); *A61M 1/3626* (2013.01); *A61M 1/73* (2021.05);
(Continued)

(58) Field of Classification Search
CPC .... A61M 1/1692; A61M 1/28; A61M 1/3626; A61M 1/73; A61M 2205/10;
(Continued)

(56) References Cited

U.S. PATENT DOCUMENTS

| | | | |
|---|---|---|---|
| 5,873,853 | A | 2/1999 | Keilman |
| 2007/0276328 | A1 | 11/2007 | Childers |

(Continued)

FOREIGN PATENT DOCUMENTS

| | | | |
|---|---|---|---|
| CN | 210785663 | U | 6/2020 |
| WO | 2022022894 | A1 | 2/2022 |

(Continued)

OTHER PUBLICATIONS

International Search Report and Written Opinion for International Application No. PCT/US2024/058243, mailed on Feb. 17, 2025, 16 pages.

(Continued)

*Primary Examiner* — John Kim
(74) *Attorney, Agent, or Firm* — KDW Firm PLLC

(57) ABSTRACT

Methods and drain systems for fluid flow monitoring and remote draining are described. In one example, the present disclosure describes a medical device drain system for monitoring, measuring, or otherwise managing the drainage of medical waste fluids, for instance, spent dialysate exiting a patient during a dialysis treatment. In some embodiments, the dialysis system may be a peritoneal dialysis (PD) system, including a gravity-based dialysis system, an APD system and/or a CAPD dialysis system. The drain system may include sensors for determining properties of the fluid drained from a patient. The drain system may include a remote liquid pump system configured to allow for pump-based draining of fluid from a patient to a drain located remote from the patient. The remote liquid pump system may be configured to receive at least one wireless signal to operate at a remote distance from the medical device. Other embodiments are described.

11 Claims, 13 Drawing Sheets

(51) Int. Cl.
*A61M 1/16* (2006.01)
*A61M 1/36* (2006.01)

(52) U.S. Cl.
CPC ... *A61M 2205/10* (2013.01); *A61M 2205/128* (2013.01); *A61M 2205/3327* (2013.01); *A61M 2205/3334* (2013.01); *A61M 2205/3375* (2013.01); *A61M 2205/3379* (2013.01); *A61M 2205/3561* (2013.01); *A61M 2205/3592* (2013.01)

(58) Field of Classification Search
CPC .... A61M 2205/128; A61M 2205/3327; A61M 2205/3334; A61M 2205/3375; A61M 2205/3379; A61M 2205/3561; A61M 2205/3592
See application file for complete search history.

(56) References Cited

U.S. PATENT DOCUMENTS

| | | | |
|---|---|---|---|
| 2014/0018727 | A1 | 1/2014 | Burbank |
| 2015/0005699 | A1 | 1/2015 | Burbank |
| 2018/0043075 | A1 | 2/2018 | Gerber |
| 2019/0262522 | A1 | 8/2019 | Wyeth |
| 2019/0358387 | A1 | 11/2019 | Elbadry |
| 2020/0405243 | A1 | 12/2020 | Yu |
| 2021/0001030 | A1 | 1/2021 | Wabel |
| 2021/0215666 | A1 | 7/2021 | Kotanko |
| 2022/0152282 | A1 | 5/2022 | Kotanko |
| 2023/0158220 | A1 | 5/2023 | Fallman |
| 2023/0173153 | A1 | 6/2023 | Silvast-Aikas |
| 2024/0009365 | A1 | 1/2024 | Jansson |

FOREIGN PATENT DOCUMENTS

| | | | |
|---|---|---|---|
| WO | 2022049208 | A1 | 3/2022 |
| WO | 2022165270 | A1 | 8/2022 |
| WO | 2022214450 | A1 | 10/2022 |
| WO | 2023122747 | A1 | 6/2023 |

OTHER PUBLICATIONS

Silencia, “Silencia—Instructions for Use,” Fresenius Medical Care, IFU-EN 07A-2022, Oct. 2022, pp. 1-292.

MEDICAL DEVICE DRAIN SYSTEM FOR MANAGING AND MONITORING WASTE MEDICAL FLUID

FIELD

The disclosure generally relates to methods and devices for medical system drain monitoring and boosting to facilitate drainage or disposal of waste medical fluids, for example, spent dialysis fluid in a peritoneal dialysis system.

BACKGROUND

Renal dysfunction or failure, for example, end-stage renal disease (ESRD), causes the body to lose the ability to remove water and minerals and excrete harmful metabolites, maintain acid-base balance, and control electrolyte and mineral concentrations within physiological ranges. Toxic uremic waste metabolites including urea, creatinine, and uric acid accumulate in the body's tissues which can result in adverse health effects if the filtration function of the kidney is not replaced. Dialysis is the typical treatment used to replace kidney function by removing these waste toxins and excess water.

The two principal dialysis methods are hemodialysis and peritoneal dialysis. During hemodialysis (HD), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

In peritoneal dialysis (PD), a dialysis solution is run through a tube (i.e., a catheter) into the peritoneal cavity, the abdominal body cavity around the intestine. The peritoneal membrane acts as a membrane for removing waste and excess water from the blood. The therapy involves phases of dialysis fluid inflow (fill), fluid dwell (dwell), and dialysis fluid outflow (drain). Different modalities of PD treatment include Continuous Ambulatory Peritoneal Dialysis (CAPD) and Automated Peritoneal Dialysis (APD). CAPD involves manually controlled fluid exchanges in which dialysis solution bags are hung or positioned, often from an IV pole, with gravity used for flowing fluid into a patient's abdomen and then drained. Devices may be used with CAPD systems to assist in fluid flow and valve control. In APD, machines (called cyclers) are designed to control the entire peritoneal dialysis process (fill, dwell and drain phases) so that it can be performed at home, usually overnight while a patient is sleeping, by automated operations. APD cyclers may provide for automated fluid pumping and control operations and/or may provide for use of gravity-based fluid flow control operations. APD cyclers can run a series of treatment cycles to implement a full treatment for a patient. The treatment typically lasts for several hours, often beginning with an initial drain procedure to empty the peritoneal cavity of used or spent dialysate. The sequence then proceeds through one or more successive cycles of fill, dwell, and drain phases for a duration or fluid volume specified by a prescription, for example, entered into the APD system.

During a dialysis treatment, spent dialysate or effluent containing the patient waste products is typically sent to a drain or a drain bag for disposal. The effluent may contain indicators of patient health, such as metabolites, toxins, and/or the like. Conventional systems for sending waste fluid to a drain during a PD treatment involve pumps or other mechanical devices arranged on the PD system. Such mechanical devices are noisy and interfere with the patient's ability to sleep during an overnight treatment. Drain bags for an overnight treatment may contain as much as 15 liters of fluid and, as such, are heavy and bulky, which makes them difficult for a patient to move them for manual draining.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In one example embodiment, a medical drain system may include a medical device having a valve coupled to a drain line adapted to drain fluid from a patient; a remote liquid pump disposed remotely from the medical device and fluidically coupled to the drain line and configured to operate to pump fluid from the patient through the drain line to a drain, wherein the remote liquid pump is configured to receive at least one wireless signal to operate at a remote distance from the medical device; and at least one fluid sensor configured to measure at least one property of the fluid flowing through the drain line.

In some embodiments of the medical drain system, the medical device may be or may include a dialysis machine.

In various embodiments of the medical drain system, the at least one fluid sensor may include an ultrasonic sensor operably coupled to the drain line to detect fluid flow in the drain line.

In some embodiments of the medical drain system, the at least one fluid sensor may include an inline fluid flow sensor operably coupled to the drain line to detect fluid flow in the drain line, the inline fluid flow sensor may include at least one projection configured to be inserted through an outer surface of the drain line to contact the fluid flowing through the drain line.

In exemplary embodiments of the medical drain system, the at least one fluid sensor may include a counter-based sensor operably coupled to the drain line to measure a volume of fluid flowing in the drain line, the counter-based sensor may be configured to detect bubbles in the fluid flowing through the drain line.

In some embodiments of the medical drain system, the medical drain system may further include a bubble creation device configured to create bubbles within the drain line at predetermined intervals for detection via the counter-based sensor.

In various embodiments of the medical drain system, the medical drain system may further include an automated valve coupled to the drain line, the automated valve may be configured to receive at least one wireless valve control signal to open or close the automated valve to regulate a flow of fluid through a portion of the drain line.

In some embodiments of the medical drain system, the medical device may transmit the at least one wireless signal to the remote liquid pump.

In exemplary embodiments of the medical drain system, the at least one fluid sensor may transmit the at least one wireless signal to the remote pump.

In some embodiments of the medical drain system, the at least one property may include one or more of a flow rate or a flow volume, and the remote liquid pump may be configured to operate to pump the fluid through the drain line to the drain when the one or more of the flow rate or the flow volume is above a threshold.

In various embodiments of the medical drain system, the medical device may be or may include a gravity-based dialysis machine, and a distal end of the drain line may be arranged at a greater height than a height of the valve of the gravity-based dialysis machine.

In one example embodiment, a method of remotely managing fluid flow in a medical drain system may include coupling a valve of a medical device to a drain line adapted to drain fluid from a patient; operating a remote pump, fluidically coupled to the drain line, to pump fluid through the drain line, wherein the remote pump is configured to receive at least one wireless signal to operate at a remote distance from the medical device; and using at least one fluid sensor to measure at least one property of a fluid flowing through the drain line to a drain.

In some embodiments of the method, the at least one fluid sensor may include an ultrasonic sensor operably coupled to the drain line to detect fluid flow in the drain line.

In various embodiments of the method, the at least one fluid sensor may include an inline fluid flow sensor operably coupled to the drain line to detect fluid flow in the drain line, the inline fluid flow sensor may include at least one projection configured to be inserted through an outer surface of the drain line to contact the fluid flowing through the drain line.

In exemplary embodiments of the method, the at least one fluid sensor may include a counter-based sensor operably coupled to the drain line to measure a volume of fluid flowing in the drain line, the counter-based sensor may be configured to detect bubbles in the fluid flowing through the drain line.

In some embodiments of the method, the bubbles may be created using a bubble creation device configured to create the bubbles within the drain line at predetermined intervals for detection via the counter-based sensor.

In various embodiments of the method, the method may further include configuring an automated valve to receive at least one wireless valve control signal to open or close the automated valve to regulate a flow of fluid through the drain line.

In some embodiments of the method, the medical device may transmit the at least one wireless signal to the remote pump.

In various embodiments of the method, wherein the at least one fluid sensor may transmit the at least one wireless signal to the remote pump.

In exemplary embodiments of the method, the at least one property may include one or more of a flow rate or a flow volume, and the remote pump may be configured to operate to pump the effluent through the drain line to the drain when the one or more of the flow rate or the flow volume is above a threshold.

In some embodiments of the method, the medical device may be or may include a gravity-based dialysis machine, and a distal end of the drain line may be arranged at a greater height than a height of the valve of the gravity-based dialysis machine.

BRIEF DESCRIPTION OF THE DRAWINGS

By way of example, specific embodiments will now be described, with reference to the accompanying drawings, in which.

DETAILED DESCRIPTION

Figure 1:
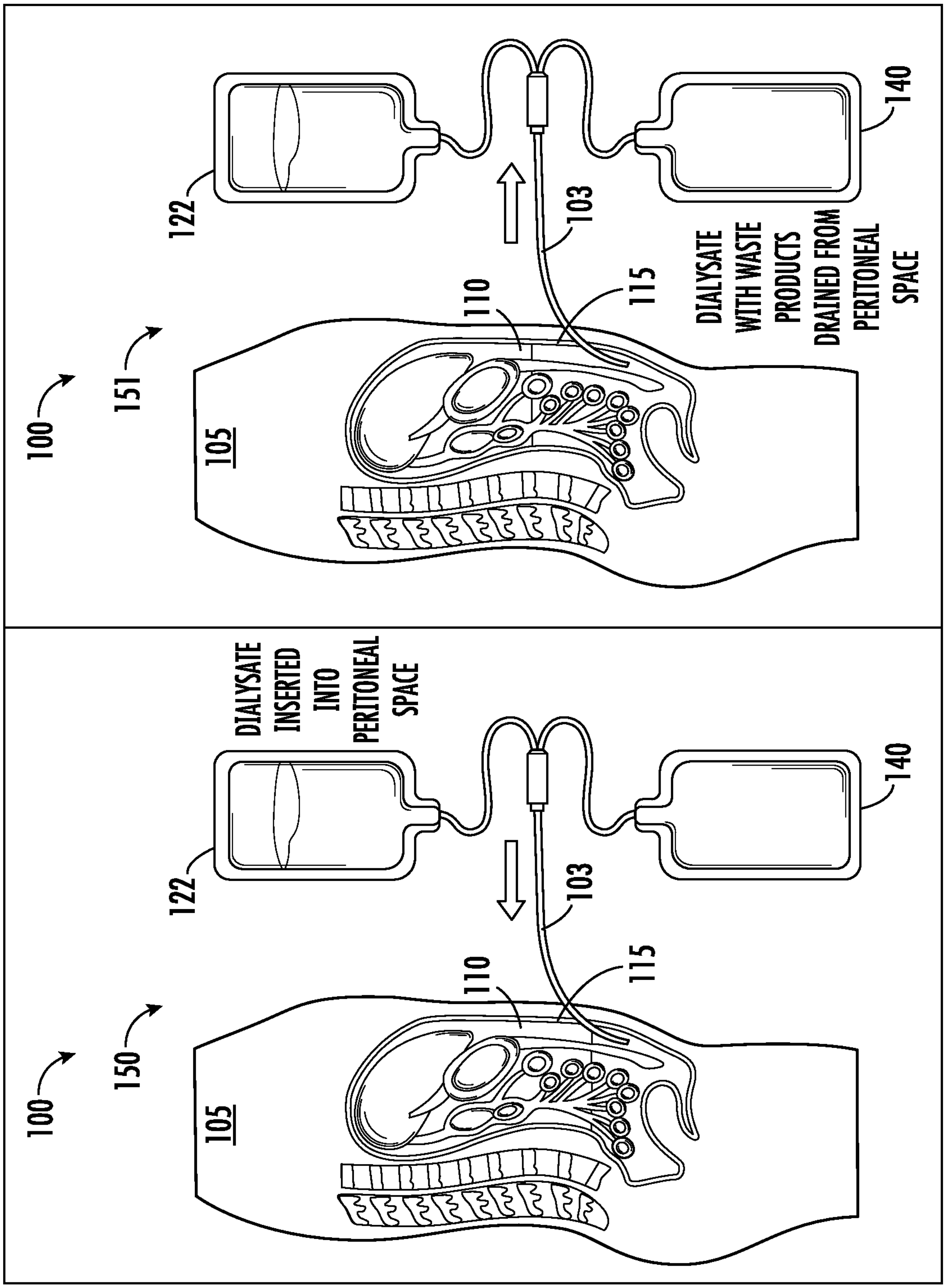
FIG. 1 illustrates an exemplary manual peritoneal dialysis (PD) process in accordance with the present disclosure.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Various features of an improved dialysis system will now be described more fully hereinafter with reference to the accompanying drawings, in which one or more features of the fluid pressure monitoring system will be shown and described. It should be appreciated that the various features may be used independently of, or in combination, with each other. It will be appreciated that a dialysis system as disclosed herein may be embodied in many different forms and should not be construed as being limited to the examples set forth herein. Rather, these examples are provided so that this disclosure will convey certain features of the dialysis system to those skilled in the art.

The present disclosure describes a dialysis drain system for monitoring, measuring, or otherwise managing the drainage of dialysis waste fluids, for instance, spent dialysate exiting a patient during a dialysis treatment. In some embodiments, the dialysis system may be a peritoneal dialysis (PD) system, including a gravity-based dialysis system, an APD system and/or a CAPD system. In some embodiments, the drain system may include devices for determining a volume of fluid drained from a patient. In various embodiments, the drain system may include a remote-pump system configured to allow for pump-based draining of fluid from a patient to a drain located remote from the patient.

Although PD systems are used in some examples herein, embodiments are not so limited, as fluid monitoring and/or draining embodiments may be used in an HD system. In addition, embodiments are not limited to use with dialysis systems, in particular, the fluid monitoring and/or draining systems may be used within numerous types of applicable systems (including non-dialysis systems) that may operate with the components of the embodiments described in the present disclosure.

FIG. 1 illustrates an exemplary manual peritoneal dialysis (PD) system 100 in accordance with the present disclosure. More specifically, FIG. 1 depicts a fill/dwell phase 150 and a drain phase 151 of a PD dialysis treatment. PD patients receive dialysis therapy in the course of filling, dwelling, and draining dialysate solution via a catheter. The dialysate solution is a liquid drug that is comprised of various salts, minerals, and sugars like dextrose or lactose. The PD catheter is implanted by a surgeon. The catheter's tubing is made from soft, flexible polyurethane or silicone and is anchored into the wall of the patient's belly or chest with a cuff (e.g., a Dacron cuff) at the exit site.

As shown in FIG. 1, the PD system 100 may include a dialysate bag 122 of dialysate fluid that is fluidically connected to a peritoneal space 110 of a patient 105 via a catheter 103 inserted through the peritoneum 115. PD treatments osmotically remove toxins from a patient's body by using the dialysate solution. The spent dialysate with urea, creatinine, water, and other waste matter (e.g., effluent) is removed from the patient into a drainage or drain bag 140.

Once the prescribed amount of effluent has been removed from the patient 105, the effluent must be discarded. Most patients either drain directly to a drain source (e.g., toilet, sink, tub, and/or the like) or to the drain bag 140. In some examples, the PD system 100 may include various valves that can be manually manipulated by a patient or other operator to control the flow of fluid into and out of the patient 105.

In addition to a manual PD system, such as the PD system 100, in some examples, a PD system may be a pump-based system (see, for example, FIGS. 3A and 3B) in which pumps are used to move the dialysate into the patient 105 and/or to pump the effluent to a drain (e.g., a drain source or the drainage bag 140). In other examples, a PD system may be a gravity-assisted or gravity-based system (see, for example, FIG. 4) in which the placement of the dialysate bag 122 (e.g., sufficiently above the peritoneal space 110) and the drain bag 140 allows gravity to pull fresh dialysate into the patent 105 and the effluent out into the drain bag 140.

Figure 2:
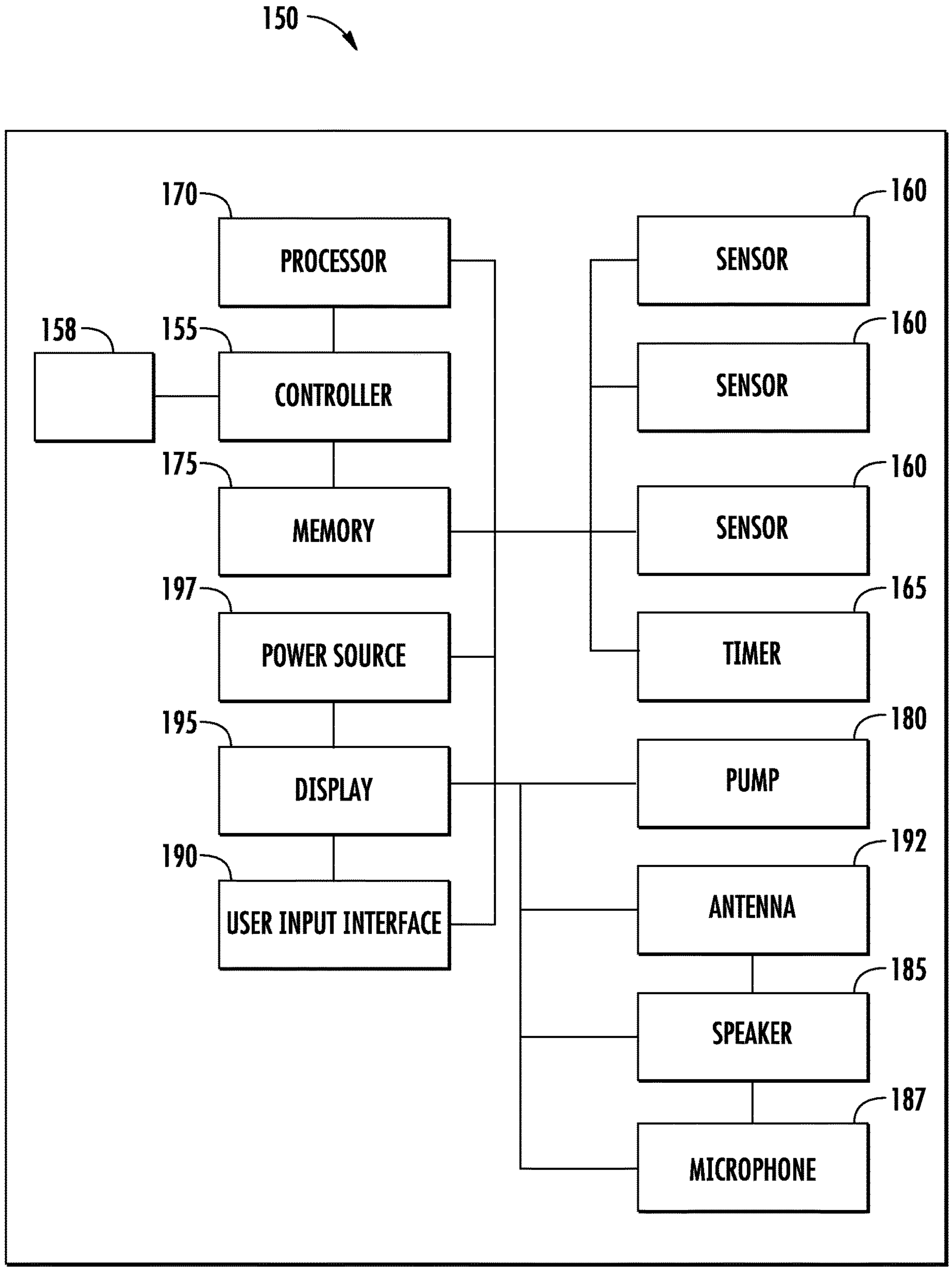
FIG. 2 illustrates an exemplary block diagram of an embodiment of a dialysis machine in accordance with the present disclosure.
Figure 5:
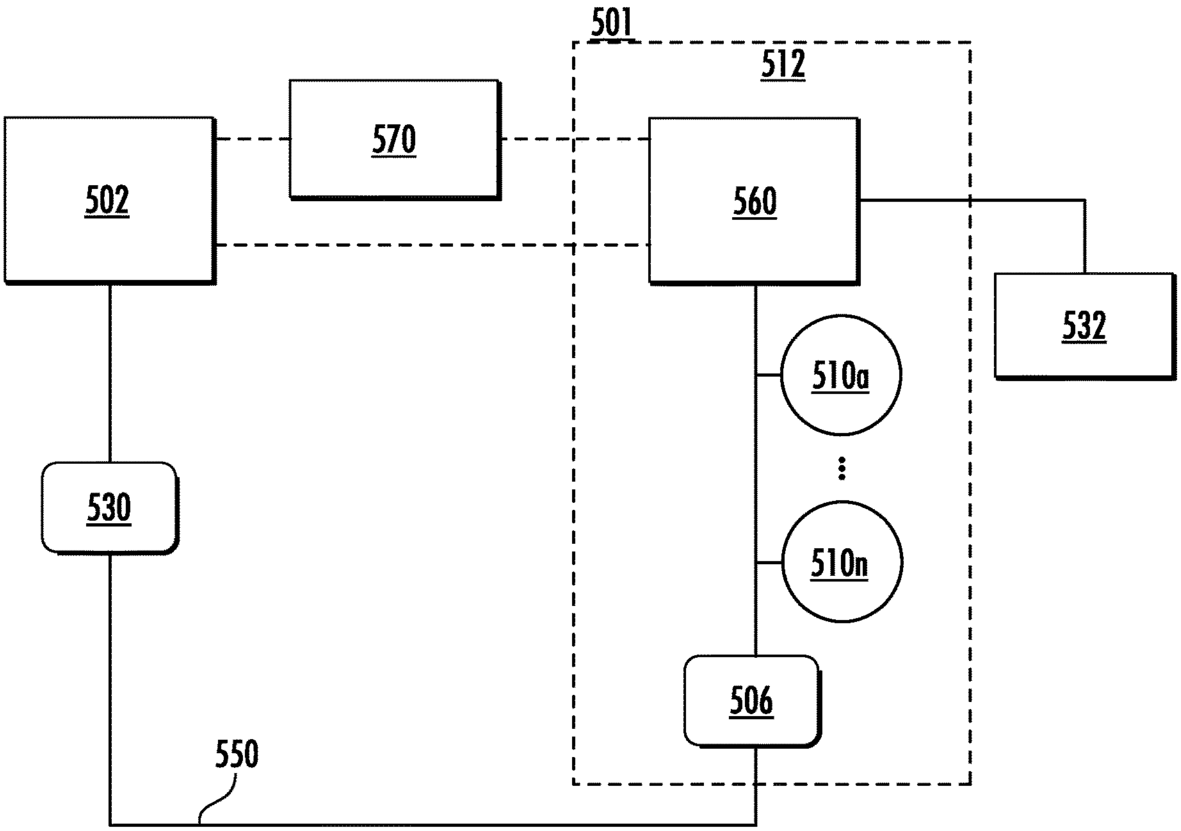
FIG. 5 illustrates an exemplary remote-drain dialysis system in accordance with the present disclosure.

FIG. 2 illustrates an exemplary block diagram of an embodiment of a dialysis machine in accordance with the present disclosure, for example, a schematic of an exemplary embodiment of a dialysis machine 150 (for instance, for dialysis system 502 of FIG. 5). The dialysis machine 150 may be a home dialysis machine, e.g., a PD machine, for performing a dialysis treatment on a patient, and may be used with the system 100 described above with respect to FIG. 1 and/or the dialysis system 502 of FIG. 5. In use, the dialysis machine 150 may include a controller 155 disposed in the dialysis machine 150. Alternatively, the dialysis machine 150 may be coupled to the controller 155, or other external systems, via a communication port or wireless communication links. The controller 155 may automatically control execution of a treatment function during a course of dialysis treatment.

The controller 155 may be operatively connected to the sensors 160 and deliver a signal to execute a treatment function (e.g., transferring dialysate from the dialysate bag 122 through the heating chamber 152 and then to the patient), or a course of treatment associated with various treatment systems. In some embodiments, a timer 165 may be included for timing the triggering of the sensors 160. The controller 155 may communicate control signals or triggering voltages to the components of the dialysis machine 150, and may include wireless communication interfaces. The controller 155 may detect remote devices to determine if any remote sensors are available to augment any sensor data being used to evaluate the patient. For example, remote devices may include fluid flow sensors, pumps (e.g., pump 560 or 960) smart phone microphones, video cameras, cameras, thermal imaging cameras, in bed sensors, sleep manager applications and sensors, web cameras, fitness sensors, stand-alone sensors, computing devices (e.g., computing device 570), and the like.

In some embodiments, the machine 150 may also include a processor 170, a memory 175, and/or the controller 155, or combinations thereof and/or the machine 150 may receive signals from the sensor(s) 160 indicating various parameters. Each fluid bag (e.g., the dialysate bags 122) may contain an approximate amount of dialysate, such that "approximate amount" may be defined as a 3 L fluid bag containing 3000 to 3150 mL, a 5 L fluid bag containing 5000 to 5250 mL, and a 6 L fluid bag containing 6000 to 6300 mL. The controller 155 may also detect connection of all fluid bags 122 connected.

Communication between the controller 155 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

In some embodiments, as will be described in greater detail below, the dialysis machine 150 may include at least one pump 180 operatively connected to the controller 155. During a treatment operation, the controller 155 may control the pump 180 for pumping fluid, e.g., fresh and spent dialysate, to and from a patient. The pump 180 may also pump dialysate from the dialysate bag 122 through, for example, the heating chamber 152.

The dialysis machine 150 may also include a user input interface 190, which may include a combination of hardware and software components that allow the controller 155 to communicate with an external entity, such as a patient or other user. These components may be configured to receive information from actions such as physical movement or gestures and verbal intonation. In some embodiments, the components of the user input interface 190 may provide information to external entities. Examples of the components that may be employed within the user input interface 190 include keypads, buttons, microphones, touch screens, gesture recognition devices, display screens, and speakers. The dialysis machine 150 may also include a display 195 and a power source 197.

In some embodiment, the user interface 190 and display 195 may be, for example, a touch screen and a control panel operable by a user (e.g., a caregiver or a patient) to allow, for example, set up, initiation, and/or termination of a dialysis treatment. The touch screen and the control panel may allow an operator to input various treatment parameters to the dialysis machine and to otherwise control the dialysis machine. In addition, the touch screen may serve as the display. The touch screen may function to provide information to the patient and/or the operator of the dialysis system. For example, the touch screen may display information related to a dialysis treatment to be applied to the patient, including information related to a prescription. The touch screen and/or display may include one or more buttons for selecting and/or entering user information.

The dialysis machine 150 may also be connectable for remote communication. For example, the dialysis machine 150 may be configured to connect to a network. The connection to network may be via a wired and/or wireless connection. In one embodiment, the dialysis machine 150 includes, for example, an antenna or other connection component 192 to facilitate connection to a network. The antenna 192 may be, for example, a transceiver for wireless connections and/or other signal processor for processing signals transmitted and received. Other medical devices (e.g., other dialysis machines) or components may be configured to connect to the network and communicate with the dialysis machine 150.

The dialysis machine 150 may also include a speaker 185 and a microphone 187. The controller 155 being operatively connected to the speaker 185 and the microphone 187.

As shown in FIG. 2, the sensors 160 may be included for monitoring parameters and may be operatively connected to at least the controller 155, the processor 170, and/or the memory 175, or combinations thereof. The processor 170 may be configured to execute an operating system, which may provide platform services to application software, e.g., for operating the dialysis machine 150. These platform services may include inter-process and network communication, file system management and standard database manipulation. One or more of many operating systems may be used, and examples are not limited to any particular operating system or operating system characteristic. In some examples, the processor 170 may be configured to execute a real-time operating system (RTOS), such as RTLinux, or a non-real time operating system, such as BSD or GNU/Linux.

In one embodiment, the processor 170 is arranged and configured to communicate with the user interface (e.g., touch screen and control panel). The processor 170 may be configured to receive data from the user interface 190 (e.g., touch screen, control panel), sensors such as, for example, weight, air content, flow, temperature, and/or pressure sensors, and control the dialysis machine 150 based on the received data. For example, the processor 170 may adjust the operating parameters of the dialysis machine 150. According to a variety of examples, the processor 170 may be a commercially available processor such as a processor manufactured by INTEL, AMD, MOTOROLA, and FREESCALE. However, the processor 170 may be any type of processor, multiprocessor or controller, whether commercially available or specially manufactured. For instance, according to one example, the processor 170 may include an MPC823 microprocessor manufactured by MOTOROLA.

The memory 175 may include a computer readable and writeable nonvolatile data storage medium configured to store non-transitory instructions and data. In addition, the memory 175 may include a processor memory that stores data during operation of the processor 170. In some examples, the processor memory includes a relatively high performance, volatile, random access memory such as dynamic random-access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 175 may include executable programs or other code that may be executed by the processor 170. The instructions may be persistently stored as encoded signals, and the instructions may cause the processor 170 to perform the functions described herein. The memory 175 may include information that is recorded, on or in, the medium, and this information may be processed by the processor 170 during execution of instructions. The memory 175 may also include, for example, specification of data records for user timing requirements, timing for treatment and/or operations, historic sensor information, and the like. The medium may, for example, be optical disk, magnetic disk or flash memory, among others, and may be permanently affixed to, or removable from, the controller 155.

The sensor(s) 160 may include a pressure sensor for monitoring fluid pressure of the machine 150, although the sensors 160 may also include any of a heart rate sensor, a respiration sensor, a temperature sensor, a weight sensor, an air sensor, a video sensor, a thermal imaging sensor, an electroencephalogram sensor, a motion sensor, an audio sensor, an accelerometer, a capacitance sensor, or any other suitable sensor. It is appreciated that the sensors 160 may include sensors with varying sampling rates, including wireless sensors.

The controller 155 may be disposed in the dialysis machine 150 or may be coupled to the dialysis machine 150 via a communication port or wireless communication links, shown schematically as communication element 158. According to various examples, the communication element 158 may support a variety of one or more standards and protocols, examples of which include USB, Wi-Fi, TCP/IP, Ethernet, Bluetooth, Zigbee, CAN-bus, IP, IPV6, UDP, UTN, HTTP, HTTPS, FTP, SNMP, CDMA, NMEA and/or GSM. As a component disposed within the machine 150, the controller 155 may be operatively connected to any of the sensors 160, the pump 180, and the like. The controller 155 may communicate control signals or triggering voltages to the components of the machine 150. As discussed, exemplary embodiments of the controller 155 may include wireless communication interfaces. The controller 155 may detect remote devices to determine if any remote sensors are available to augment any sensor data being used to evaluate the patient.

Figure 3A:
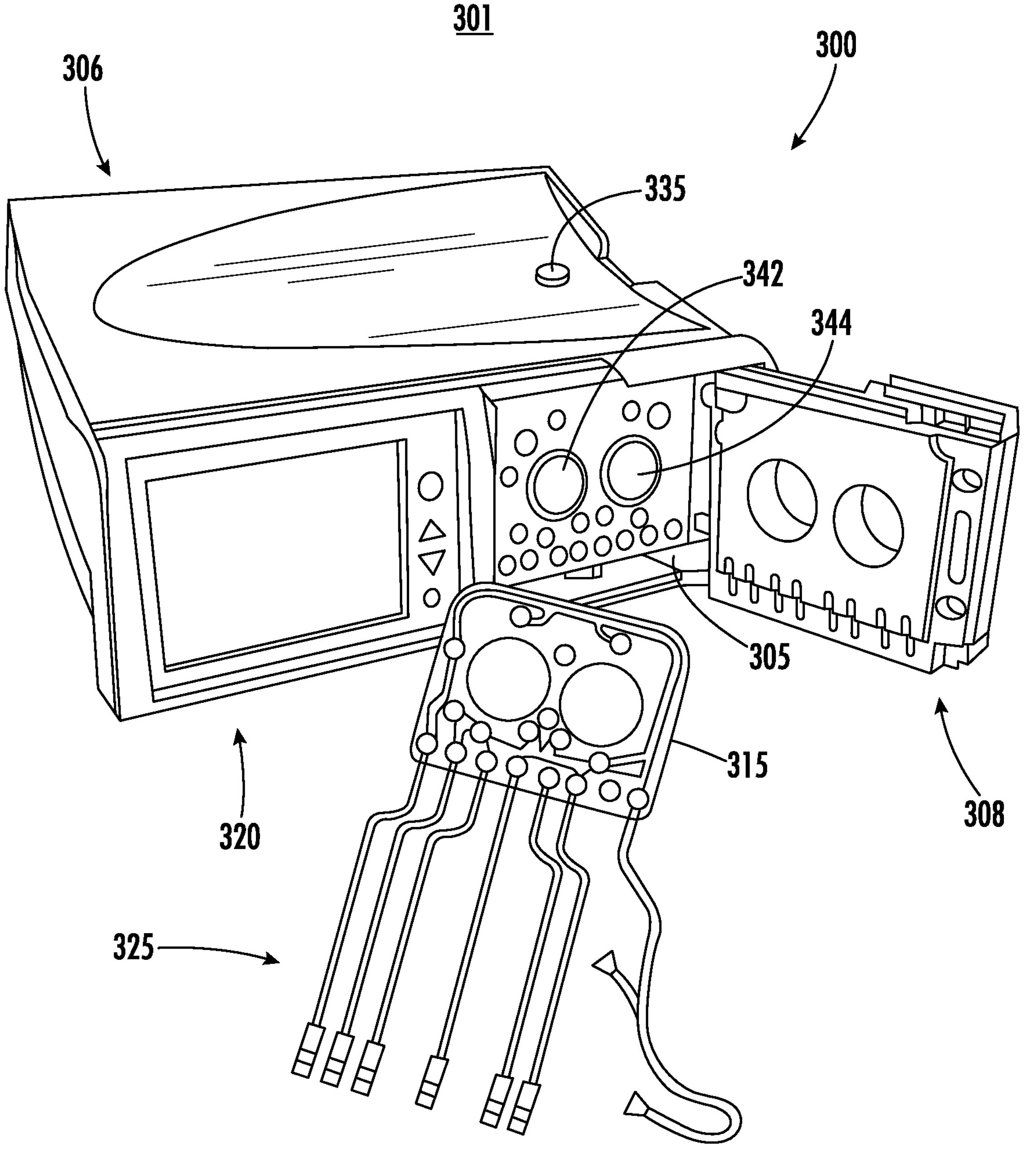
FIGS. 3A and 3B illustrate an exemplary PD system in accordance with the present disclosure.
Figure 3B:
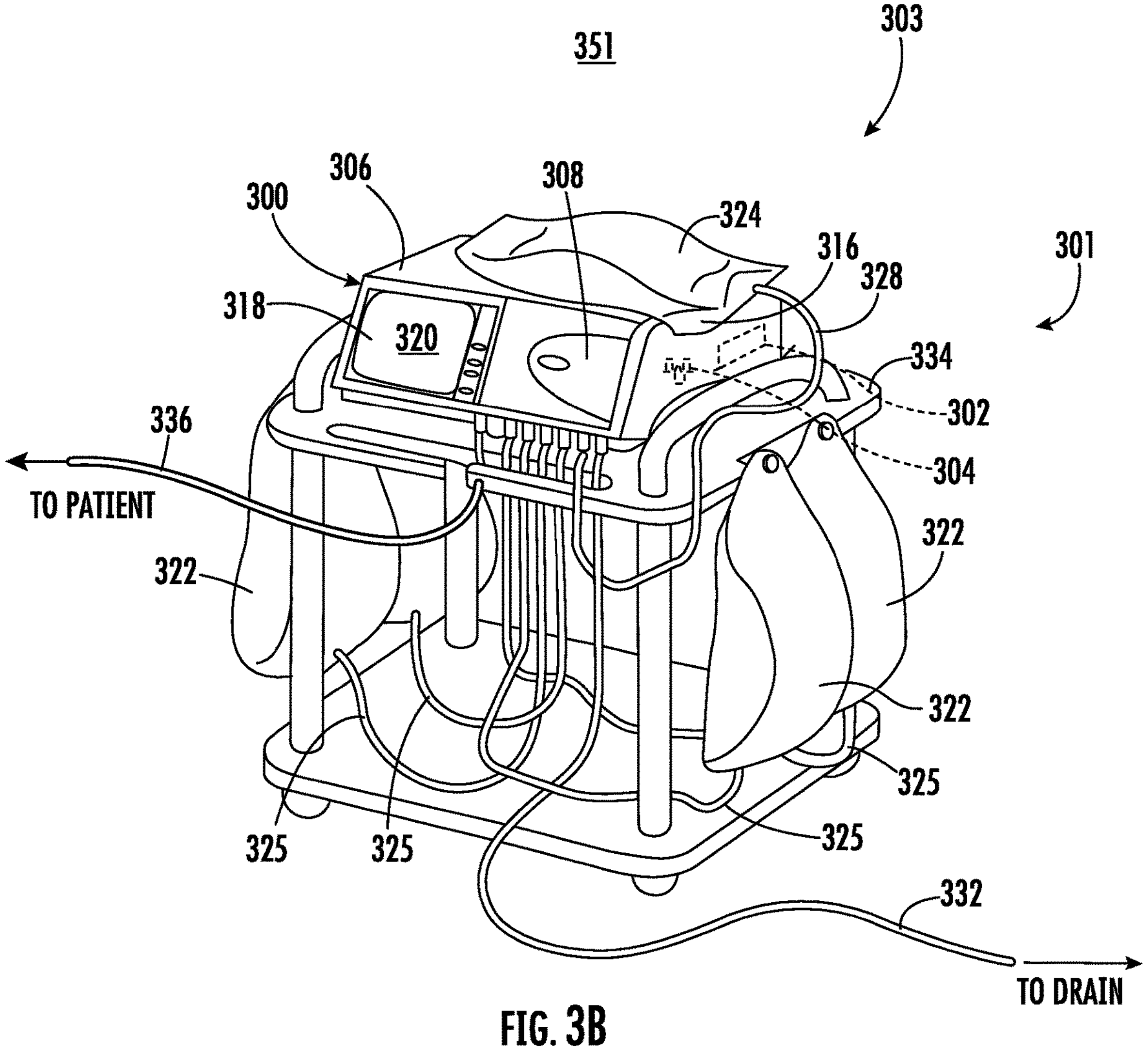

FIGS. 3A and 3B show an example of a PD system 301 (e.g., a pump-based PD system), which is configured in accordance with an exemplary embodiment of the system described herein. In some implementations, the PD system 301 may be a home PD system, e.g., a PD system configured for use at a patient's home. The dialysis system 301 may include a dialysis machine 300 (e.g., a peritoneal dialysis machine 300, also referred to as a PD cycler) and in some embodiments the machine may be seated on a cart 334.

The dialysis machine 300 may include a housing 306, a door 308, and a cartridge interface including pump heads 342, 344 for contact with a disposable cassette, or cartridge

315, where the cartridge 315 is located within a compartment formed between the cartridge interface and the closed door 308 (e.g., cavity 305). Fluid lines 325 may be coupled to the cartridge 315 in a known manner, such as via a connector, and may further include valves for controlling fluid flow to and from fluid bags, including fresh dialysate and warming fluid. In another embodiment, at least a portion of the fluid lines 325 may be integral to the cartridge 315. Prior to operation, a user may open the door 308 to insert a fresh cartridge 315 and to remove the used cartridge 315 after operation.

The cartridge 315 may be placed in the cavity 305 of the machine 300 for operation. During operation, dialysate fluid may flow into a patient's abdomen via the cartridge 315, and spent dialysate, waste, and/or excess fluid may be removed from the patient's abdomen via the cartridge 315. The door 308 may be securely closed to the machine 300. Peritoneal dialysis for a patient may include a total treatment of approximately 10 to 30 liters of fluid, where approximately 3 liters of dialysate fluid are pumped into a patient's abdomen, held for a period of time, e.g., about an hour (the dwell duration), and then pumped out of the patient. This is repeated until the full treatment volume is achieved, and may, for example, occur overnight while a patient sleeps.

A heater tray 316 may be positioned on top of the housing 306. The heater tray 316 may be any size and shape to accommodate a bag of dialysate (e.g., a 5-liter (L) bag of dialysate) for batch heating. The dialysis machine 300 may also include a user interface such as a touch screen 318 and control panel 320 operable by a user (e.g., a caregiver or a patient) to allow, for example, set up, initiation, and/or termination of a dialysis treatment. In some embodiments, the heater tray 316 may include a heating element 335 for heating the dialysate prior to delivery into the patient.

Dialysate bags 322 may be suspended from hooks on the sides of the cart 334, and a heater bag 324 may be positioned on the heater tray 316. Hanging the dialysate bags 322 may improve air management as air content may be disposed by gravity to a top portion of the dialysate bag 322. Although four dialysate bags 322 are illustrated in FIG. 3B, any number "n" of dialysate bags may be connectable to the dialysis machine 300 (e.g., 3 to 5 bags, or more), and reference made to first and second bags does not limit the total number of bags used in a dialysis system 301. For example, the dialysis machine may have dialysate bags 322*a*, . . . 322*n* connectable in the system 301. In some embodiments, connectors and tubing ports may connect the dialysate bags 322 and lines for transferring dialysate. Dialysate from the dialysate bags 322 may be transferred to the heater bag 324 in batches. For example, a batch of dialysate may be transferred from the dialysate bags 322 to the heater bag 324, where the dialysate is heated by the heating element 335. When the batch of dialysate has reached a predetermined temperature (e.g., approximately 98°-100 °F, 37 °C), the batch of dialysate may be flowed into the patient. The dialysate bags 322 and the heater bag 324 may be connected to the cartridge 315 via dialysate bag lines or tubing 325 and a heater bag line or tubing 328, respectively. The dialysate bag lines 325 may be used to pass dialysate from dialysate bags 322 to the cartridge 315 during use, and the heater bag line 328 may be used to pass dialysate back and forth between the cartridge and the heater bag 324 during use. In addition, a patient line 336 and a drain line 332 may be connected to the cartridge 315. The patient line 336 may be connected to a patient's abdomen via a catheter and may be used to pass dialysate back and forth between the cartridge and the patient's peritoneal cavity by the pump heads 342, 344 during use. The drain line 332 may be connected to a drain or drain receptacle and may be used to pass dialysate from the cartridge to the drain or drain receptacle during use.

Although in some embodiments, dialysate may be batch heated as described above, in other embodiments, dialysis machines may heat dialysate by in-line heating, e.g., continuously flowing dialysate through a warmer pouch positioned between heating elements prior to delivery into a patient. For example, instead of a heater bag for batch heating being positioned on a heater tray, one or more heating elements may be disposed internal to the dialysis machine. A warmer pouch may be insertable into the dialysis machine via an opening. It is also understood that the warmer pouch may be connectable to the dialysis machine via tubing (e.g., tubing 325), or fluid lines, via a cartridge. The tubing may be connectable so that dialysate may flow from the dialysate bags, through the warmer pouch for heating, and to the patient.

In such in-line heating embodiments, a warmer pouch may be configured so dialysate may continually flow through the warmer pouch (instead of transferred in batches for batch heating) to achieve a predetermined temperature before flowing into the patient. For example, in some embodiments the dialysate may continually flow through the warmer pouch at a rate between approximately 300-300 mL/min. Internal heating elements (not shown) may be positioned above and/or below the opening, so that when the warmer pouch is inserted into the opening, the one or more heating elements may affect the temperature of dialysate flowing through the warmer pouch. In some embodiments, the internal warmer pouch may instead be a portion of tubing in the system that is passed by, around, or otherwise configured with respect to, a heating element(s).

The touch screen 318 and the control panel 320 may allow an operator to input various treatment parameters to the dialysis machine 300 and to otherwise control the dialysis machine 300. In addition, the touch screen 318 may serve as a display. The touch screen 318 may function to provide information to the patient and the operator of the dialysis system 301. For example, the touch screen 318 may display information related to a dialysis treatment to be applied to the patient, including information related to a prescription.

The dialysis machine 300 may include a processing module 302 that resides inside the dialysis machine 300, the processing module 302 being configured to communicate with the touch screen 318 and the control panel 320. The processing module 302 may be configured to receive data from the touch screen 318 the control panel 320 and sensors, e.g., weight, air, flow, temperature, and/or pressure sensors, and control the dialysis machine 300 based on the received data. For example, the processing module 302 may adjust the operating parameters of the dialysis machine 300.

The dialysis machine 300 may be configured to connect to a network 303. The connection to network 303 may be via a wired and/or wireless connection. The dialysis machine 300 may include a connection component 304 configured to facilitate the connection to the network 303. The connection component 304 may be a transceiver for wireless connections and/or other signal processor for processing signals transmitted and received over a wired connection. Other medical devices (e.g., other dialysis machines) or components may be configured to connect to the network 303 and communicate with the dialysis machine 300.

The user interface portion such as the touch screen 318 and/or control panel 320 may include one or more buttons for selecting and/or entering user information. The touch screen 318 and/or control panel 320 may be operatively connected to a controller (not shown) and disposed in the machine 300 for receiving and processing the inputs to operate the dialysis machine 300.

Dialysis system 301 depicted in FIGS. 3A and 3B may be the same or similar to the Liberty® Cycler produced by Fresenius Medical Care North America of Waltham, Massachusetts, United States of America. However, embodiments are not so limited, as FIGS. 3A and 3B depict an illustrative dialysis system according to one example. Embodiments may include, use, or be used in combination with various types of dialysis systems currently known to persons of skill in the art or developed in the future, including PD systems.

Figure 4:
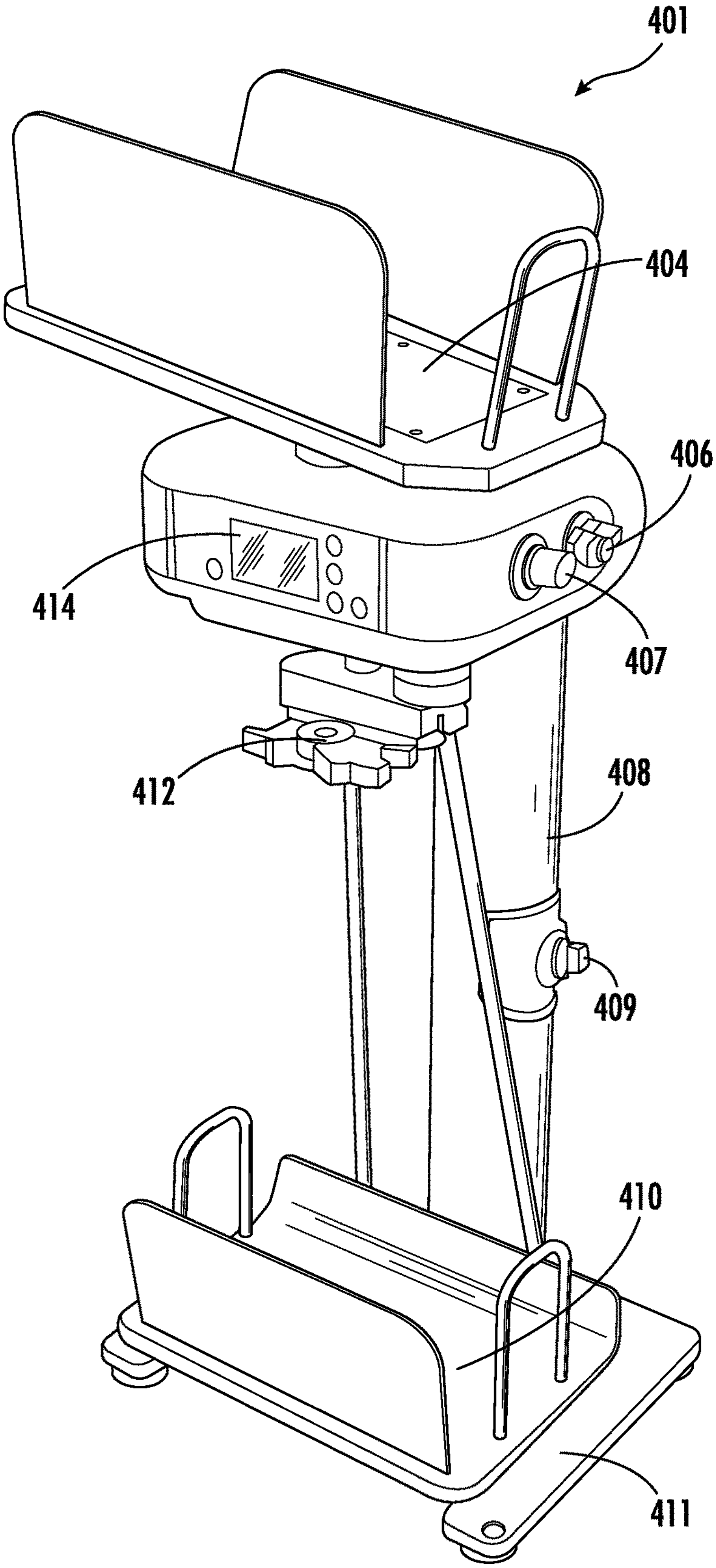
FIG. 4 illustrates an exemplary gravity-based PD system in accordance with the present disclosure.

FIG. 4 illustrates an exemplary gravity-based PD system in accordance with the present disclosure. As shown in FIG. 4, a gravity-based PD system 401 may include a heating tray 404 configured to hold and heat fresh dialysate bags arranged at a top of a mounting stand 408. Inflow valves 406 and 407 may be configured to regulate the flow of dialysate from the dialysate bags to the patient, for example, according to a prescription entered into a control system or element 414. A drain valve 409 may be configured to regulate the flow of the dialysate from the patient to a drain bag arranged on a drain tray 410 arranged, for example, on a pedestal located at a base of the mounting stand 408. The drain bag may be fluidically connected to the patient via flexible tubing coupled to a clip or organizer 412 used to hold patient connectors, tubing, and/or the like and to facilitate simple and secure connection and disconnection of the patient to the PD system 401.

The dialysis system 401 depicted in FIG. 4 may be the same or similar to the Silencia® system produced by Fresenius Medical Care. However, embodiments are not so limited, as FIG. 4 depicts an illustrative dialysis system according to one example. Embodiments may include, use, or be used in combination with various types of dialysis systems currently known to persons of skill in the art or developed in the future, including gravity-based PD systems.

The PD system 401 is a gravity-based PD cycler that, unlike automated peritoneal dialysis (APD) devices (e.g., PD system 201), uses no pumps to fill or drain the PD patient because gravity alone is used to move fluid into and out of the patient. The PD system 401 operates similar to the manual PD system 150 of FIG. 1, however, the PD system 401 includes automatic control via control element 414, for example, to automatically open and close valves (e.g., valves 406, 407, and/or 409) or clamps on the fresh dialysate line and the effluent (waste dialysate) line and keeps track of fluid movement by weighing fresh dialysate bags (on the tray 404) and/or effluent collection (drain) bags (on the tray 410).

In some embodiments, tray 404 and/or tray 410 may include weight sensors configured to weigh dialysate and/or drain bags arranged thereon. The control element 414 may be configured to determine the volume of fluid that has left a dialysate bag on the tray 404 (and, therefore, has been infused into the patient) based on a change in weight of the dialysate bag. The control element 414 may be configured to determine the volume of fluid that has drained from the patient based on a change in weight of a drain bag on the tray 410.

For example, a prescription may require that the patient be diffused with 1.5 L of dialysate. The control element 414 may receive weight information from the tray 404 indicating the weight of a dialysate bag arranged on the tray 404. The control element 414 may be operative to calculate the volume of dialysate that has been infused into the patient from the dialysate bag based on the change in weight of the dialysate bag (e.g., a decrease in weight of the dialysate bag correlates to an increase in the volume of fluid that has been infused into the patient). The control element 414 can control valves 406 and/or 407 based on the volume information calculated based on the weight of the dialysate bag. For example, valve 406 and/or 407 can be closed responsive to the weight of the dialysate bag indicating that 1.5 L of fluid has been infused into the patient.

CAPD therapy and gravity-based cyclers require effluent drained from the patient to be temporarily stored in a drain bag, for example, as a storage mechanism and/or so that the effluent can be weighed to determine how much additional fluid was removed by ultrafiltration, a key marker of therapy efficacy. An overnight treatment may require draining multiple liters of fluid (for example, from about 5 L to about 15 L). As a result, the drain bags will be heavy and bulky when it is time to lift them to a drain for manually drainage. Even if the patient could drain directly from the peritoneal cavity to a drain, the drain will typically never be as high as a countertop sink because gravity cannot move the fluid to higher level. Draining a CAPD set directly to a drain is cumbersome, requiring the patient or care partner to carry the entire CAPD set to a tub to drain it or lift it up to a countertop height to drain it into a sink. The CAPD drain bag weighs five pounds and is drained by cutting open the bag and spilling its contents of toxins like urea and ammonia, mixed with dialysate.

APD cyclers can send effluent directly to a drain like a toilet or tub via a long drain tube so there are no effluent bags for the patient to manage. However, conventional APD cyclers require pumps and/or other mechanical devices to be located directly adjacent to the patient in order to pump away the contents of the drainage bags. Part of the appeal of gravity-based cyclers is that they are quiet because they can operate without a pump to produce noise.

Accordingly, some embodiments provide a drain volume monitoring system configured to monitor the volume of dialysis fluids, such as the volume of a fluid drained from a patient during a dialysis treatment. In this manner, pumpless dialysis systems (such as PD system 501) can operate without requiring the weighing of drain bags to determine patient fluid drain volume.

In addition, some embodiments provide a remote drain (or pump-boost) system configured to facilitate pump-based movement of dialysis waste fluid using a pump that is sufficiently far away from the patient to reduce or even eliminate the negative noise effects of conventional pump-based dialysis systems. Furthermore, the remote-drain system may make it easier for patients to use or travel with PD systems, including gravity-based systems. For example, a patient may only have to use the main dialysis unit with the heating tray (i.e., without the pillar and drain tray). When setting up the remote drain system, the patient would place the main unit on a sideboard or something else of a certain height to ensure that gravity works for filling the patient. The remote drain (or pump boost) device would work in tandem with the gravity-based PD control unit by counting the drain volume and closing the drain valve/clamp when draining has stopped. Accordingly, eliminating the hanging scale for gravity-based PD devices with the portable remote drain device according to some embodiments would make the whole PD system lighter, smaller, easier to transport and set up, and less costly and complex and allow convenient draining anywhere (with reduced or even eliminated noise due to the remote location of the pump).

FIG. 5 illustrates an exemplary remote-drain (or pump boost) dialysis system in accordance with the present disclosure. As shown in FIG. 5, a dialysis remote drain system may include a dialysis system 502 fluidically coupled to a patient to provide dialysis treatment. In some embodiments, the dialysis system 502 may be a PD system. A drain line 550 may fluidically couple the dialysis system 502 with a remote-drain system 512. In some embodiments, the remote-drain system 512 may include a pump or pump system 560. The pump 560 may be configured to force spent dialysate or effluent from a drain source 530 to a drain 532. In various embodiments, the drain 532 may be or may include one or more of a toilet, a bathtub, a sink, or any other plumbing fixture.

In some embodiments, the drain source 530 may be a patient (i.e., a catheter or other conduit coupled to the patient), a drain bag, drain line or circuit, and/or the like. In various embodiments, one or more sensors 510*a-n* may be coupled to or otherwise associated with the drain line 550 to monitor for fluid flow and/or for use in determining a volume of fluid moving through a portion of the drain line 550. The sensors 510*a-n* may include various types of devices for measuring properties of the fluid, for example, which can be used to determine a volume of fluid that has drained from a patient. For example, the sensors 510*a-n* may be able to determine a flow rate for fluid flowing through a fluid conduit, such as drain line 550.

In various embodiments, a sensor 510*a-n* may include a flow sensor. A non-limiting example of a flow sensor is an ultrasonic flow sensor. In one example, an ultrasonic flow sensor may be configured to fit around the drain line 550 tubing to monitor effluent drained from the patient as it flows by, directly to the drain. For example, a fluid sensor could be designed into a clip-based or otherwise lockable enclosure to ensure proper fit over the disposable tubing. An illustrative ultrasonic flow sensor is an FD-X Series Clamp-On flow sensor provided by the Keyence Corporation of Osaka, Japan. An ultrasonic flow sensor may be configured to detect flow and/or to measure the volume of effluent drained, which may provide a more accurate measurement of the therapy than effluent weight alone (for example, because effluent does not weigh exactly the same as the fresh dialysate). For example, an ultrasonic flow sensor on a gravity-based cycler detecting a flow rate of 200 ml/min for ten minutes would lead to a calculation that 2000 ml has been drained from the patient.

Although the sensors 510*a-n* are positioned between the drain source 530 and the pump 560, embodiments are not so limited as one or more of the sensors 510*a-n* may be positioned along various portions of a fluid line, including the drain line 550. For example, a flow sensor can be arranged between a fresh dialysate bag and the dialysis system 502 to accurately measure inflow and outflow (for instance, without the use of a weight sensor).

Figure 6:
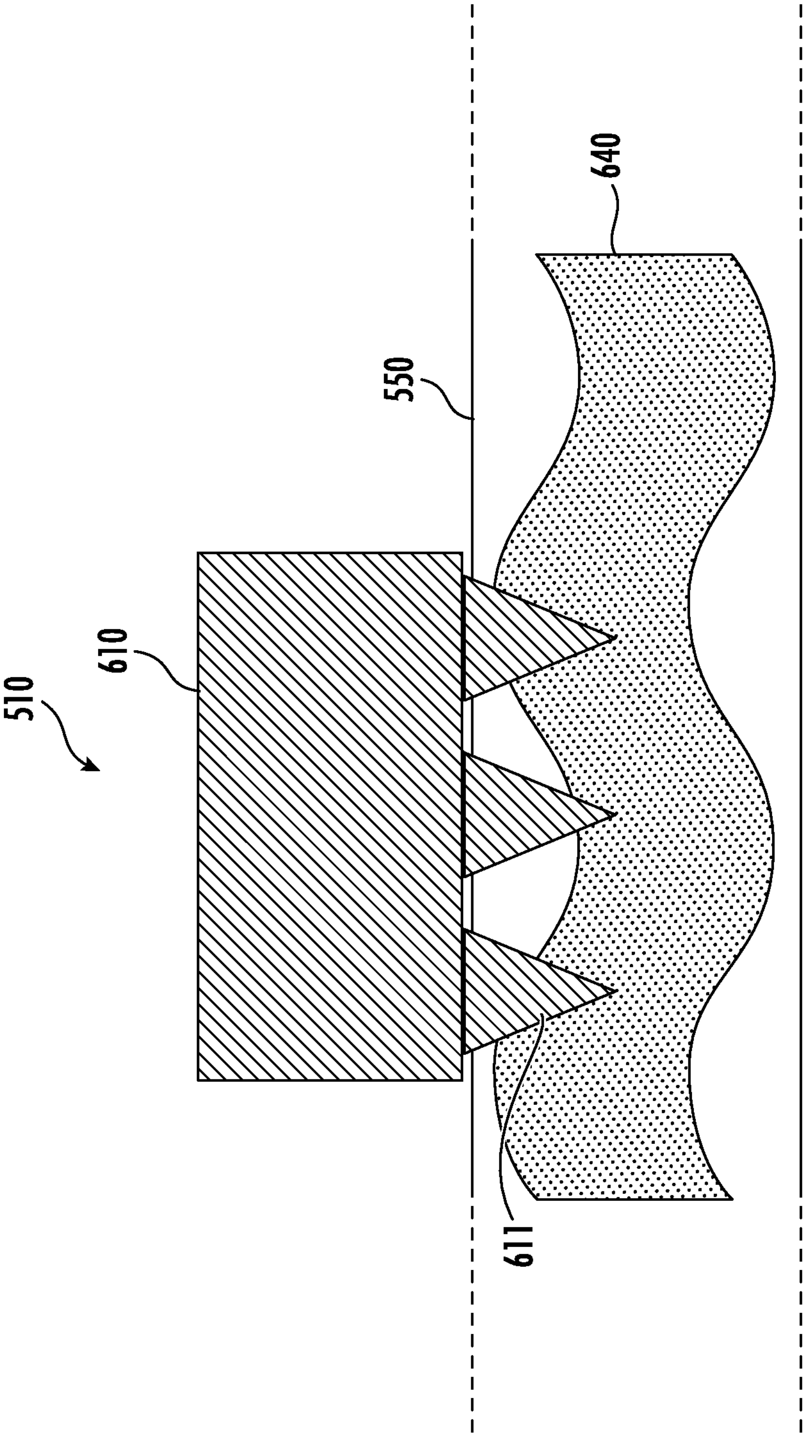
FIG. 6 illustrates an exemplary fluid sensor in accordance with the present disclosure.

In another example, a flow sensor may be an inline fluid flow sensor. FIG. 6 illustrates an exemplary fluid sensor in accordance with the present disclosure. As shown in FIG. 6, a sensor 510 may include a housing 610 and one or more protrusions 611 may be sharp and configured to pierce the flexible, polymer surface of the drain line 550 (or other fluid tubing), for instance, if pushed against the outer surface of the drain line 550 with sufficient force. For example, a closure lever or other tool could be used to apply the sensor 510 with the necessary force. The holes resulting from the piercing of the protrusions 611 may be small enough to prevent leaks. The sensor 510 of FIG. 6 may be configured as a disposable inline sensor that could be configured for the fluid 640 to make direct contact with its contact points (protrusions 611). For example, the protrusions 611 may be spikes that make small piercings into the disposable drain tubing 550 to make direct contact with the fluid 640 inside.

The protrusions 611 may be configured to contact fluid 640 flowing through the drain line 550. In various embodiments, one or more sensor devices for various properties may be associated with the sensor 510. Non-limiting examples of sensor devices may include a fluid flow sensor, a temperature sensor, and/or a conductivity sensor. The sensor 510 may be configured as a dual channel "all-in-one" sensor for measuring multiple properties. In various embodiments, the sensor modules may be arranged on the protrusions 611 (i.e., the protrusions 611 are sensor contact points) or, in other embodiments, the protrusions 611 may allow for the fluid 640 to enter the body 610 wherein the sensor modules are stored. In various embodiments, instead of including protrusions 611 that pierce into the tubing 550, the sensor 510 and the tubing 550 may be a contiguous, for instance, with the sensor 510 formed or affixed within or on a portion of the tubing 550. Additional measurement modalities, such as temperature and conductivity, may facilitate analysis of dialysis effluent, for example, for determining infection, peritonitis, and/or the like.

Figure 7:
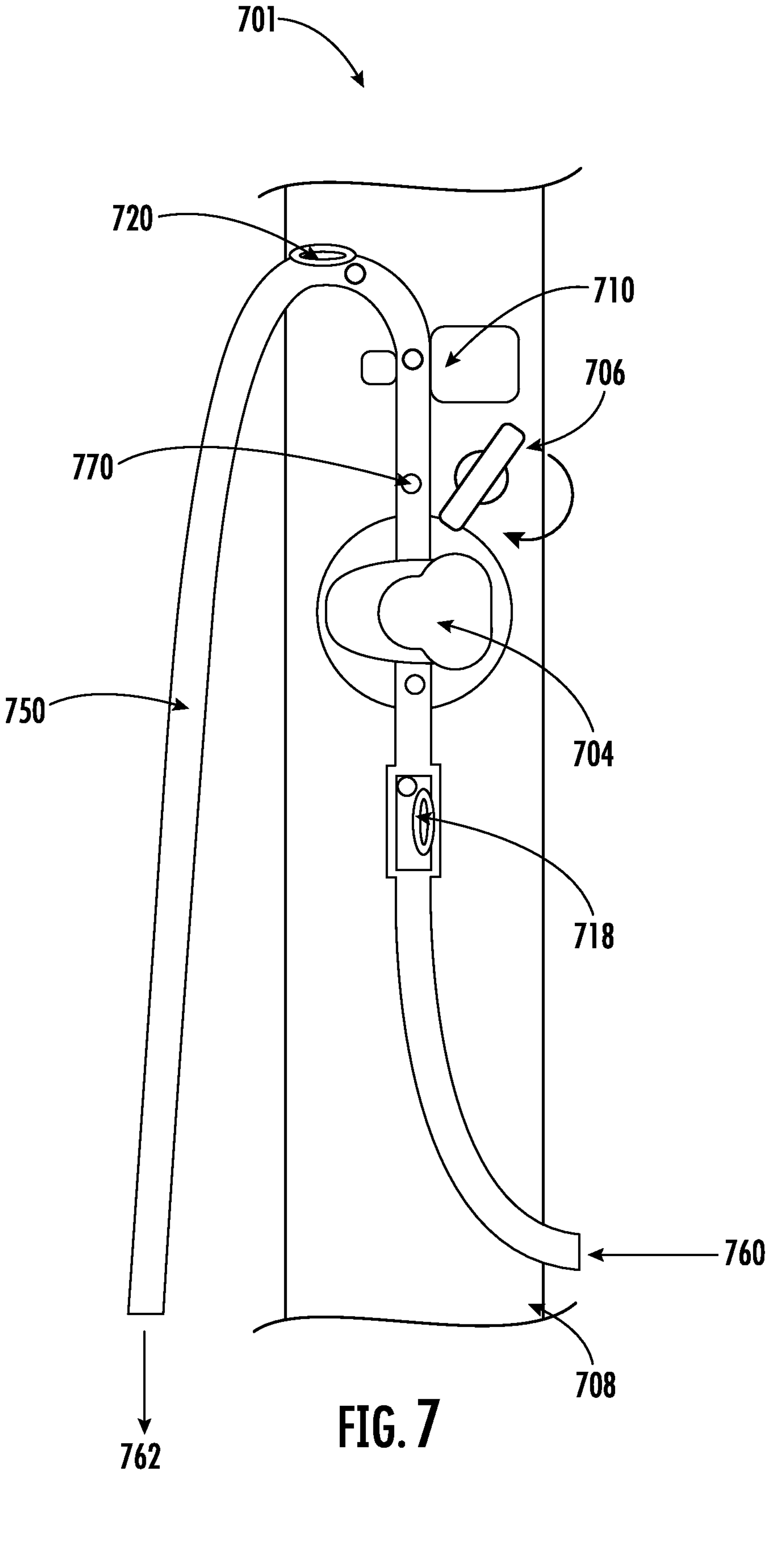
FIG. 7 illustrates an exemplary bubble-generating fluid sensor system in accordance with the present disclosure.

In a further example, a sensor 510*a-n* may include a counter-based sensor to sense bubbles or other elements in the fluid. FIG. 7 illustrates an exemplary bubble-counter sensor system in accordance with the present disclosure. As shown in FIG. 7, a bubble-counter sensor system 701 may include a bubble creation device 706 configured to create bubbles 770 within fluid tubing 750.

In various embodiments, the fluid tubing 750 may be a drain line (e.g., drain line 550), for instance, for fresh dialysate entering the dialysis system 502. In some embodiments, fluid tubing 750 may be coupled to a portion of the dialysis system 502, such as a pillar 708 (e.g., mounting stand 308). In some embodiments, a drain line valve or clamp 704 may be operative to regulate fluid flow through the fluid tubing 750.

In some embodiments, the bubble creation device 706 may be a vibration device or other device configured to create bubbles at predetermined, regular intervals (e.g., every X ml, every X seconds, and/or the like). A sensor 710 downstream from the bubble creation device 706 may be operative to count the bubbles, for instance, based on differences between the fluid and the bubbles, including, without limitation, light absorbance, refraction, opaqueness, and/or the like. In some embodiments, the sensor 710 may be an optical sensor, an ultrasound sensor, a light sensor, and/or the like. One or more vents 720 may be located upstream of the sensor 710 to allow the bubbles 770 to evacuate after being counted.

A dialysis system or a computing device (for instance, dialysis machine 150 or computing device 570) may be configured to receive the number of bubbles and a corresponding measurement value, such as a distance value, a volume value, a time value and/or the like to determine a volume of effluent based on a known bubble/measurement value relationship. For example, if the bubble creation device 706 is configured to make one air bubble every second and the flow rate is 300 ml/min (5 ml/second), then if 10 bubbles are counted, a calculation that a volume of 50 ml of fluid have been drained (e.g., passed the sensor) may be determined. In another example, the bubble creation device 706 may be configured to generate one bubble every milliliter of fluid flow; if 10 bubbles are counted, then a calculation that a volume of 10 ml of fluid have been drained (e.g., passed the sensor) may be determined. Other bubble/measurement value relationships may be used with the bubble-counter sensor system 701.

Figure 8B:
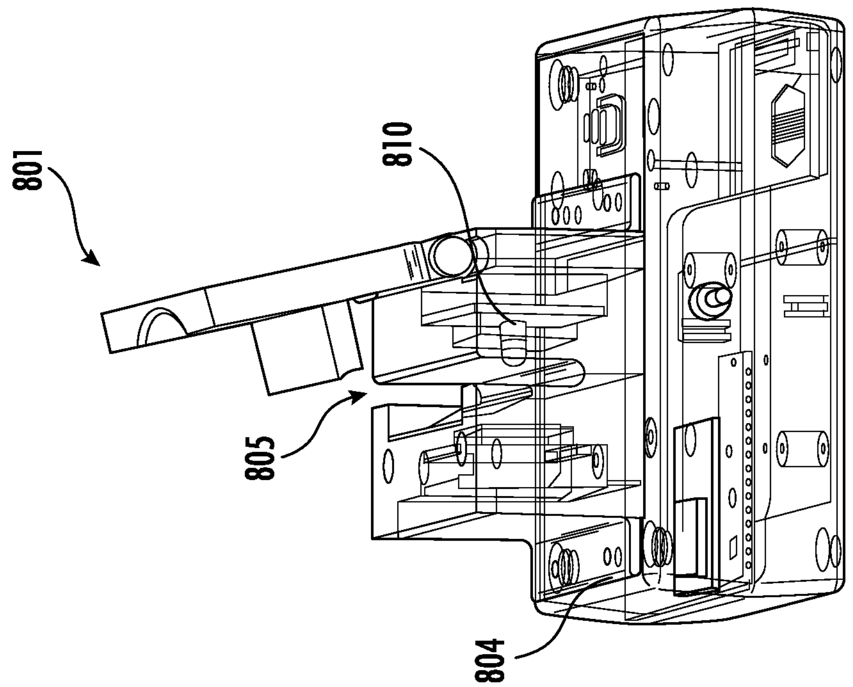
FIGS. 8A and 8B illustrate an exemplary turbidity meter in accordance with the present disclosure.
Figure 8A:
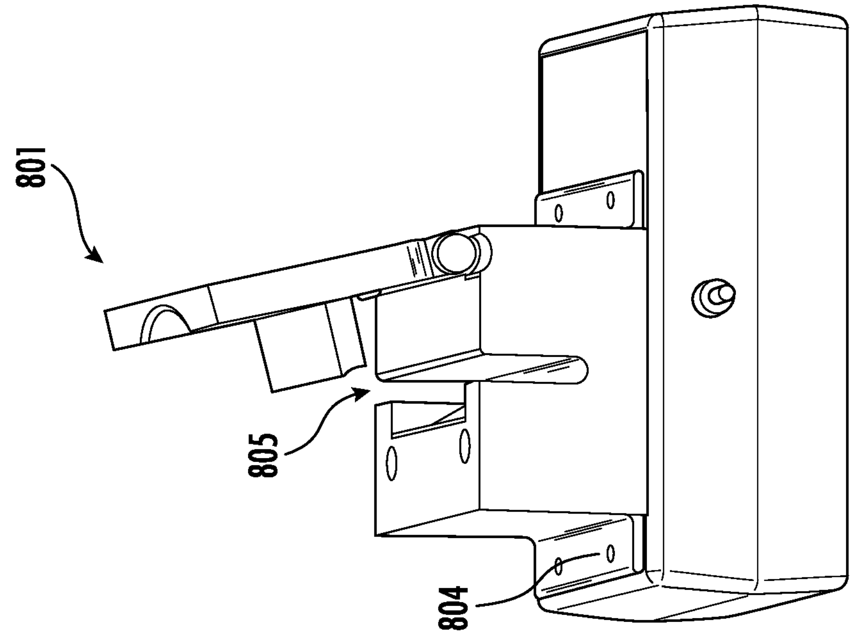

In some embodiments, the sensors 510*a-n* may include various sensors to measure turbidity. FIGS. 8A and 8B illustrate an exemplary turbidity sensor system in accordance with the present disclosure. More specifically, FIG. 8A depicts a front, perspective view of a turbidity meter 801 and FIG. 8B depicts an internal view of the turbidity meter 801. In some embodiments, a turbidity meter 801 may include housing 804 with a channel 805 formed therein. The channel 804 may be configured for tubing to be arranged within the turbidity meter 801. Tubing arranged within the channel 805 may be analyzed by a turbidity sensor 810. For example, turbidity sensor 810 may be configured to measure the "cloudiness" or the amount of light that is scattered by the suspended solids in water to determine a turbidity value for patient effluent. In some embodiments, one or more of the various sensors 410*a-n* may be arranged in or on the housing 804, for example, to allow for the simultaneous measurement of fluid flow, turbidity, and/or other properties in a single measurement unit (e.g., the turbidity meter 801 housing 804). Monitoring and analyzing turbidity in spent dialysate may be beneficial in the early detection of peritonitis. A non-limiting example of an optical-based turbidity sensor that may be used in connection with the system described herein is described in U.S. Patent Application Publication No. 2022/0152282 to Kotanko et al., entitled "Systems and Methods for Analyzing Spent Dialysate," the entire contents of which are incorporated herein by reference.

In some embodiments, a sample bag or other fluid container may be arranged in the drain line 550 to collect fluid for testing or other purposes. In one example, a sample bag may be arranged via a valve/clamp T-connection. In various embodiments, the sample bag may be connected to the drain tubing 550 with the valve/clamp in between to prevent contamination and be reused until a sample is actually collected. If the turbidity meter 801 detects cloudiness (e.g., a turbidity reading over a threshold value), the sample bag could be filled automatically so that the patient can bring it to the clinic to have it checked. The dialysis system would then alert the patient that the sample bag was filled (and the reason that it was filled).

Referring to FIG. 5, in exemplary embodiments, one or more valves, clamps, or other devices 506 may be arranged along the drain line 550 to control the flow of fluid through the drain line 550. In some embodiments, one or more of the valves 506 may be manual valves operated by a patient or other operator. In various embodiments, one or more of the valves 506 may be automatically controlled by the dialysis system 502 or a computing device (for instance, dialysis machine 150 or computing device 570).

In some embodiments, at least a portion of the drain system 512 may be remote from the patient (relative to conventional drain bags and/or the like that are adjacent to the patient with the dialysis system). For example, the dialysis system 502 may be adjacent to a patient in their bedroom or living room, and the drain system 512 or a portion thereof (for instance, the pump 560, such as a liquid pump) is located in a bathroom. In some embodiments, a distance (a "remote distance") between the patient (or dialysis system 502) and the pump 560 may be about 3 feet, about 5 feet, about 10 feet, about 15 feet, about 30 feet, about 50 feet, about 100 feet, or about any value or range between any two of these values (including endpoints). In various embodiments, the remote distance may be about 5 feet to about 20 feet, about 10 feet to about 30 feet, or equal to or greater than 20 feet. In some embodiments, the pump 560 may have sufficient power (e.g., watt capacity) to pump fluid over the distance through a drain line, such as flexible tubing having a diameter of about 10 mm to about 100 mm. In various embodiments, the pump 560 may be a peristaltic pump.

In some embodiments, the liquid pump 560 may be configured to wirelessly communicate with various devices or systems. For example, the pump 560 may wirelessly communicate with the dialysis system 502 or a computing device 570. Wireless communication may be performed via various communication protocols and/or networks, including, without limitation, an Internet network, a wireless local area network (LAN), a cellular network, a Personal Communication Service, a Personal Area Network, Wireless Application Protocol, Multimedia Messaging Service, Enhanced Messaging Service, Short Message Service, Wi-Fi, Fixed Wireless Data, IEEE 802.11 family of networking protocols, Bluetooth, NFC, Radio Frequency Identification (RFID), Wi-Fi, and/or the like.

The pump 560 may include hardware, transceivers, software, firmware, memory, processing devices, and/or the like to implement wireless communication and signal processing according to various embodiments. For instance, the pump 560 may include a one or more processors and a memory device storing instructions for processing signals from the dialysis system 502, the sensors 510*a-n*, and/or the computing device 570 for performing the functions described according to some embodiments, such as turning on/off, controlling the flow rate, providing instructions, information, and/or other signals to the dialysis system 502 and/or the computing device 570.

Operational aspects of the pump 560 may be controlled via the dialysis system 502 and/or the computing device 570 through wireless communication. For example, the computing device 570 may be a smart phone, tablet computing device, laptop, personal computer, workstation, and/or the like operated by the patient or other operator. The computing device 570 may have a software application installed for controlling various operational functions of the pump 560, for instance, starting/stopping the pump 560, flow control, and/or the like. In various embodiments, the computing device 570 software application may be configured to control one or more of the valves 560.

In some embodiments, a patient or other user may control operation of the pump 560 through direct communication between the pump 560 and the computing device 570. In other embodiments, the user may send control signals or other instructions from the computing device 570 to the dialysis system 502, and the dialysis system 502 communicates the instructions wirelessly to the pump 560.

Figure 9:
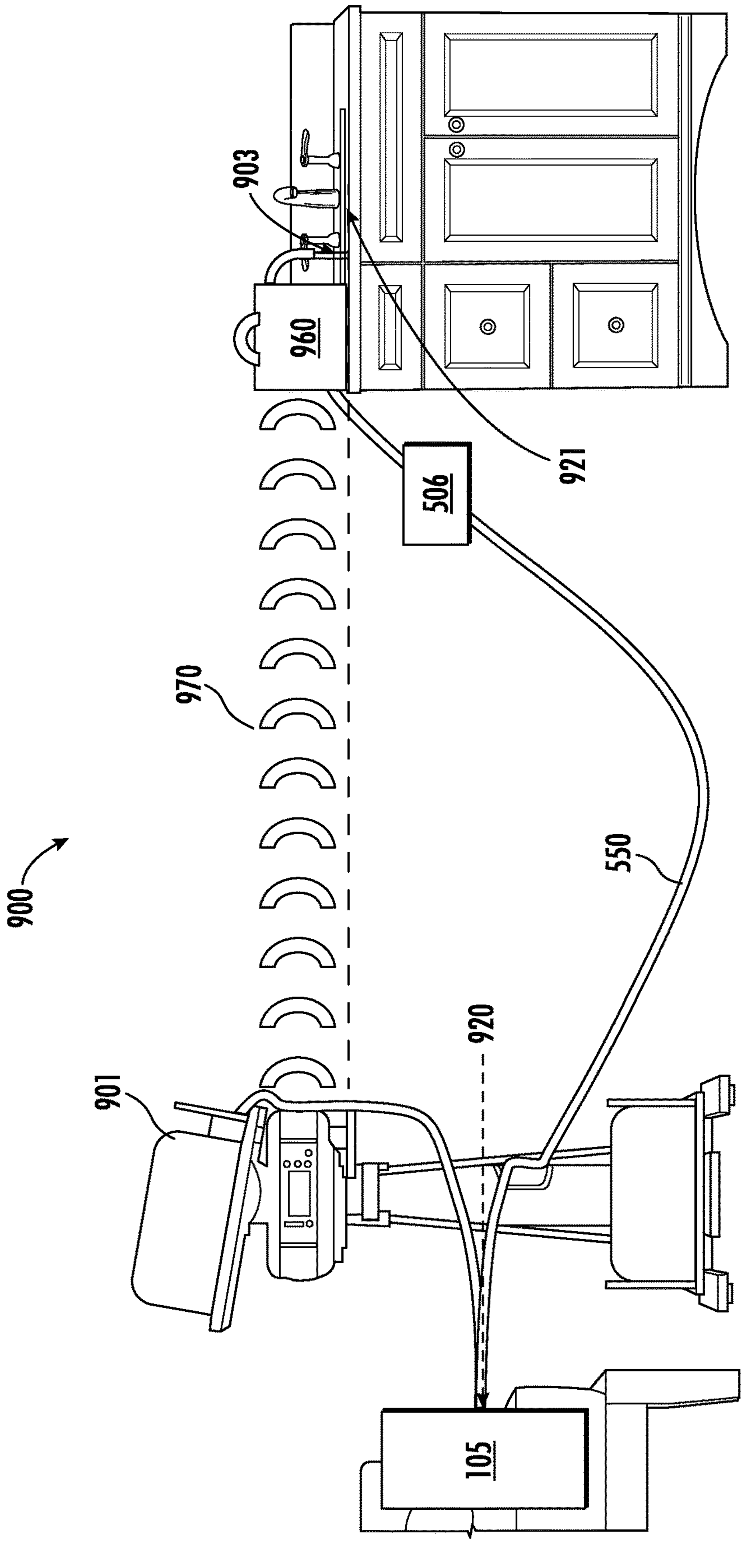
FIG. 9 illustrates an exemplary PD system using a remote-drain system in accordance with the present disclosure.

FIG. 9 illustrates an exemplary PD system using a remote-drain system in accordance with the present disclosure. As shown in FIG. 9, a dialysis system 900 may include a dialysis machine 901 fluidically coupled to a patient 105 to provide a PD dialysis treatment to the patient 105. In some embodiments, the dialysis machine 901 may be a gravity-based dialysis machine, an APD dialysis machine, a CAPD dialysis system, and/or the like. The dialysis machine 901 (or, alternatively, a computing device, such as the computing device 570) may be configured to wirelessly communicate 970 with a pump 960, such as a liquid pump. The liquid pump 960 may be fluidically coupled to a drain line 550, for example, for patient effluent resulting from draining of spent dialysate from the patient 105 during a PD treatment. The pump 960 may be configured to transfer fluid from the drain line 550 to a drain 903, such as a sink or other similar drain source.

The liquid pump 960 may be remotely located from the patient 105, for example, about 5 to about 20 feet from the patient 105 (and in another room). Because the pump 960 is located a remote distance from the patient 105, the noise generated by the pump that is noticeable by the patient 105 is reduced, and may be completely eliminated. The pump 960 may also include sound-dampening or noise cancelling features to further facilitate the noise-reduction effects. In addition, the use of a remote pump 960 allows for different drain heights, for example, when compared with conventional gravity-based PD systems. Height 920 is the maximum drain height with a conventional PD system, for instance, a gravity-based PD system. However, an elevated drain height 921 (e.g., a height higher than a patient or drain source, such as a drain bag or drain fluid outlet of a dialysis machine) may be used with a PD system using the remote pump 960 due to the enhanced fluid pumping capabilities achieved by the pump 960.

Figure 10:
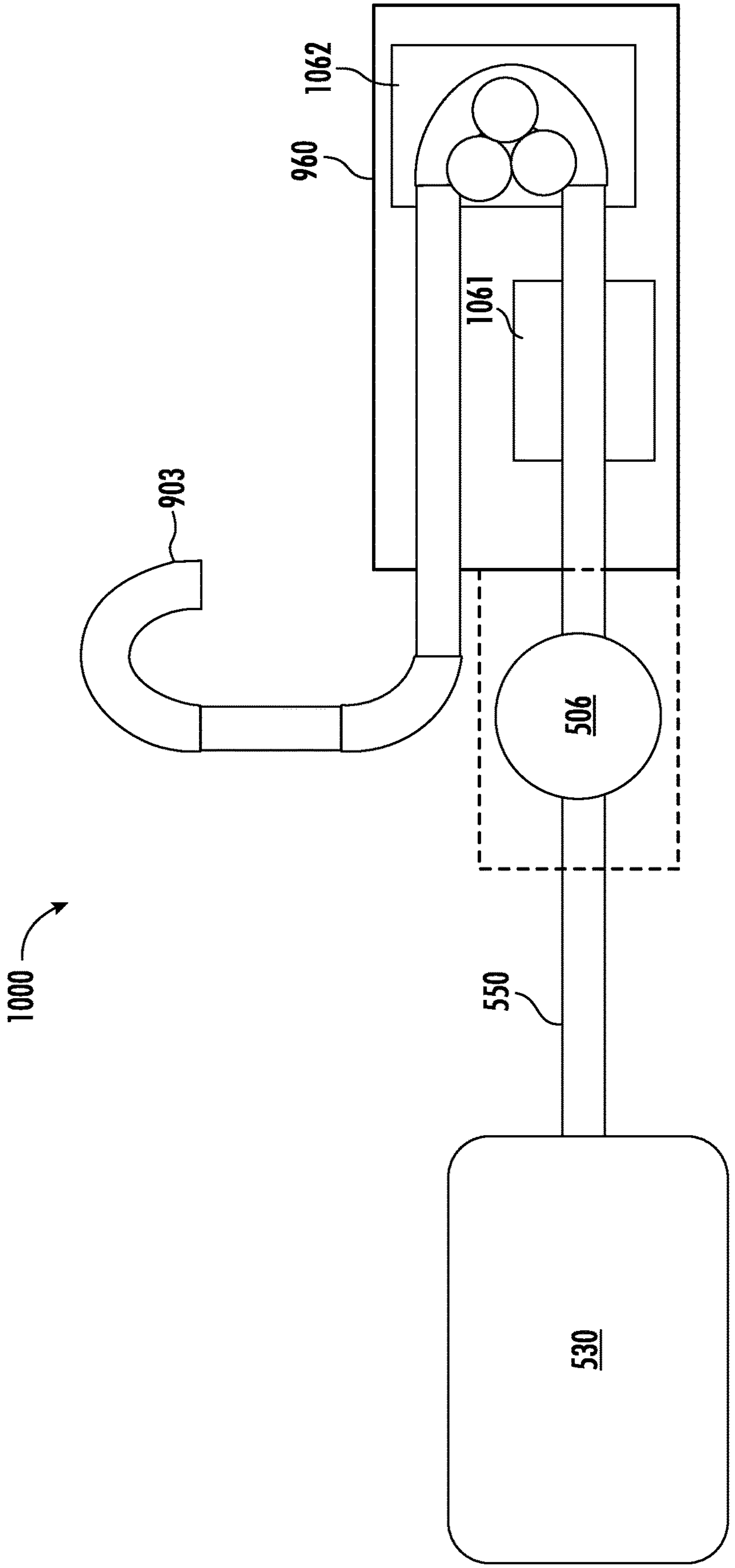
FIG. 10 illustrates an exemplary remote-drain system in accordance with the present disclosure.

FIG. 10 illustrates an exemplary remote-drain pump system in accordance with the present disclosure. As shown in FIG. 10, the liquid pump 960 may include a pump device 1062, which is the specific device for pumping fluid within the system of the pump 960. In some embodiments, the pump device 1062 may be or may include a peristaltic pump, although this is for illustrative purposes, as other types of pump devices 1062 may be used. The pump 960 may be configured to engage dialysis system fluid tubing, such as a drain line 550 from a drain source 530. The pump 960 may be configured to pump fluid in the drain line 550 to a drain 903. In some embodiments, a sensor 1061 may be included in or arranged on the drain line, for instance, sensor 610 or a clip-on ultrasonic flow sensor.

In various embodiments, a valve 406 may be configured to control the flow of fluid through the drain line 550 before the pump 960. In some embodiments, the valve 506 may be remotely controlled by the dialysis system 502 and/or the computing device 570 (see, for example, FIGS. 11A-11D). The pump 960 and/or components thereof may be battery-powered (including rechargeable batteries) and/or could be powered via being plugged into a standard power outlet. The liquid pump 960 may be used with fluid lines for different types of dialysis systems or tubing sets, including a gravity-based dialysis system, an APD dialysis system, a CAPD dialysis system, and/or the like.

For a CAPD system, a tubing set may be used that includes a fresh dialysate bag and y-connector with a short drain line connected to disposable/reusable drain line. In some embodiments, a patient or other operator could either select via an application (e.g., running on a dialysis machine 150 and/or a computing device 570, such as a smartphone application) to start draining. In various embodiments, the operator may select via the application to operate an automated clamp (see, for example, FIGS. 11A-11D) that, when opened, indicates to a connected device (e.g., pump 960) that pumping may automatically commence. In some embodiments, via the application, an operator may set a desired flow rate, stop/stop flow, and/or other various operating parameters.

Figure 11A:
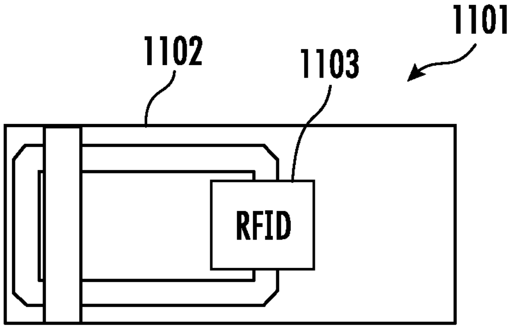
FIGS. 11A-11D illustrate an exemplary automated drain line clamp in accordance with the present disclosure.
Figure 11B:
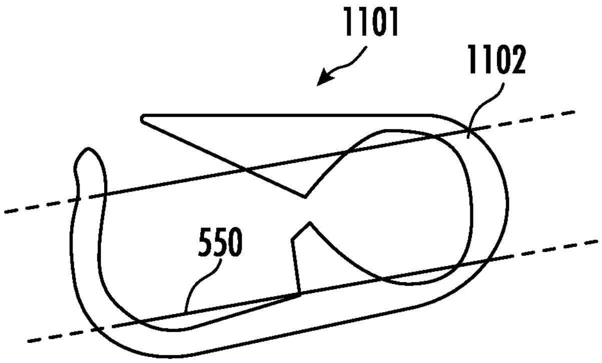
Figure 11C:
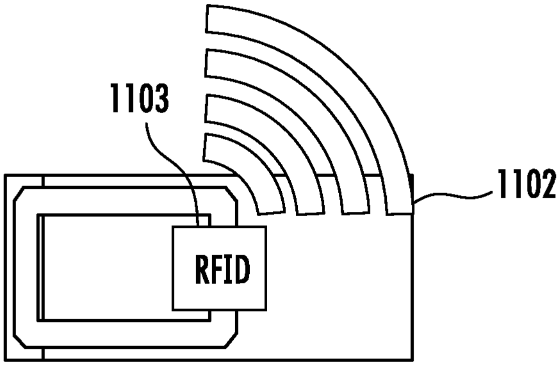
Figure 11D:
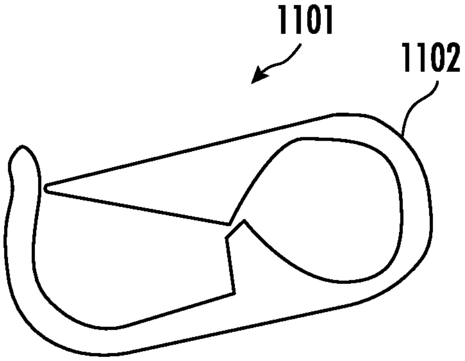

FIGS. 11A-11D illustrate an exemplary automated valve or clamp in accordance with the present disclosure. More specifically, FIGS. 11A and 11B depict a top and side view, respectively, of an automated valve or clamp 1101 in an open position (e.g., allowing the flow of fluid through a drain line 550 or other tubing), and FIGS. 11C and 11D depict a top and side view, respectively, of the automated clamp 1101 in a closed position. In some embodiments, the automated clamp 1101 may include a body 1102 coupled to a signal receiver 1103 to receive signals for opening/closing the automated clamp 1101. One non-limiting example of a signal receiver 1103 is a radio frequency identification (RFID) module or chip set. For example, when the signal receiver receives a signal (e.g., an electrical signal) from a device, such as the dialysis system 502, the computing device 570, the pump 960, and/or the like, the automated clamp 1101 may be closed. In the absence of the signal, the automated clamp 1101 may be open. The automated clamp 1101 may include a mechanical device for applying force to open/close the automated clamp 1101. Non-limiting examples of mechanical devices may include a mechanical actuator, a rotary actuator, a servo motor, and/or the like. In some embodiments, one or more of clamps 506 may be or may include automated clamp 1101. In various embodiments, automated clamp 1101 may operate as an automated valve, including any valve disclosed in the present disclosure (e.g., valve 406, etc.).

Referring to FIG. 9, for a gravity-based PD system, the dialysis machine 901 may be wirelessly linked 970 to the pump 960 device situated, for instance, about 5 to about 20 feet away from the dialysis machine 901. When the dialysis machine 901 opens the valve/clamp 406 to initiate the drain phase, it would signal to the PD drain boost device to start pumping. The flow of fluid may be sensed via the sensor 510 (for instance, an ultrasonic flow sensor clamped around, or otherwise in engagement with, the drain line 550). The pump 960, the dialysis system 502, and/or the computing device 570 may be configured to monitor the flow rate to measure the drain volume and to pump the effluent via the pump device 1062 to the drain 903.

When flow is no longer detected in the drain line 550 or the flow has reached a minimum rate as determined via the liquid pump 960, the dialysis system 502, and/or the computing device 570, a signal may be generated to close the drain pathway from the patient 105.

In some embodiments, if the dialysis treatment is in the final or only exchange, any fluid remaining in the fresh dialysate bag may be sent directly to the drain, as the remainder of the fluid in the drain line may be completely evacuated by running the pump 960 at a high rate.

In various embodiments, if a drain bag scale is used or to drain directly to bags (for instance, for effluent analysis), the pump 960 be used as an aid in emptying drain bags wherever they are located by connecting a drain line with the pump 960 to the drain bags. In other embodiments, if the drain line is longer than can be handled by the pump 960), a second disposable or durable tubing length may be connected to the outlet at the pump 960 because the pump 960 produces the necessary pressure to overcome the additional distance to the drain.

In some embodiments, the pump 960 may read pressure on the drain line 550 to ensure pressure on the patient 105 remains minimal. In some embodiments, pressure monitoring external to the drain line 550 tubing may be performed via one or more sensing systems, including, without limitation an ultrasonic system, a photonic radar system, and/or the like.

Figure 12:
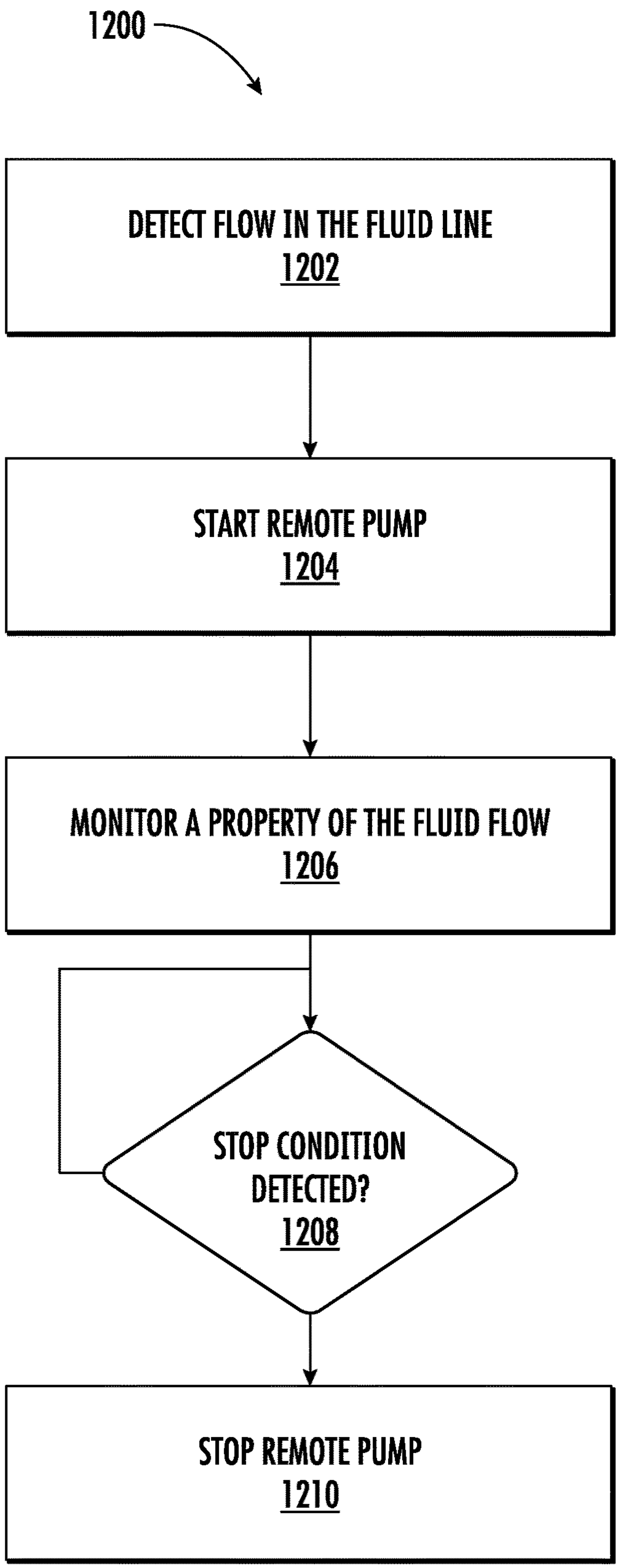
FIG. 12 illustrates a flow diagram of an example of a method of controlling fluid flow in a dialysis system according to one or more embodiments of the present disclosure.

FIG. 12 illustrates a flow diagram of an example of a method of controlling fluid flow in a dialysis drain system according to one or more embodiments of the present disclosure. At step 1202, fluid flow may be detected in a fluid line fluidically coupled to a remote (or boost) pump. For example, fluid flow due to draining of patient effluent in the drain line 550 may be measured by a sensor 510*a-n*, such as an ultrasonic sensor, communicatively coupled to the dialysis system 502, the pump 560, and/or the computing device 570. In some embodiments, detection of fluid flow may be determined based on the opening of a valve, such as a drain valve opened by a dialysis machine.

The remote liquid pump for drainage may be started at step 1204. For example, the detection of fluid flow may cause dialysis system 502, the pump 560, and/or the computing device 570 to provide a signal to the pump 560 (particularly, the pump device 1062) to become activated to pump fluid. At step 1206, a property of the fluid flow may be monitored. For example, a sensor 510*a-n* may monitor for the fluid flow rate, fluid volume that has flowed through a portion of the drain line 550 (or other conduit, including dialysate inflow tubing), and/or other fluid flow properties.

A stop condition may be monitored at step 1208. For example, hardware or a software application of the dialysis system 502, the pump 560, and/or the computing device 570 may monitor for a stop condition, such as a fluid flow rate below a threshold, a maximum volume, and/or the like. When the stop condition has been detected (e.g., the flow rate is below a threshold, a maximum volume of fluid has flowed through a portion of the fluid conduit, and/or the like), a signal may be provided to the pump 560 (or more particularly to the pump device 1062) to stop the pump 560 at step 1210. In addition, the stop condition may cause other functions, such as the opening/closing of associated valves.

The system described herein has been explained in connection dialysis machines having a particular configuration. It is contemplated that the system described herein may be used with dialysis machines having other configurations, for example, different types of dialysis machines and/or dialysis machines having drain systems.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A medical drain system, comprising:

a medical device having a valve coupled to a drain line adapted to drain fluid from a patient;

a remote liquid pump disposed remotely from the medical device and fluidically coupled to the drain line and configured to operate to pump fluid from the patient through the drain line to a drain, wherein the remote liquid pump is configured to receive at least one wireless signal to operate at a remote distance from the medical device; and at least one fluid sensor configured to measure at least one property of the fluid flowing through the drain line.

2. The medical drain system of claim 1, wherein the medical device is a dialysis machine.

3. The medical drain system of claim 1, wherein the at least one fluid sensor comprises an ultrasonic sensor operably coupled to the drain line to detect fluid flow in the drain line.

4. The medical drain system of claim 1, wherein the at least one fluid sensor comprises an inline fluid flow sensor operably coupled to the drain line to detect fluid flow in the drain line, the inline fluid flow sensor comprising at least one projection configured to be inserted through an outer surface of the drain line to contact the fluid flowing through the drain line.

5. The medical drain system of claim 1, wherein the at least one fluid sensor comprises a counter-based sensor operably coupled to the drain line to measure a volume of fluid flowing in the drain line, the counter-based sensor configured to detect bubbles in the fluid flowing through the drain line;

the medical drain system further comprising a bubble creation device configured to create bubbles within the drain line at predetermined intervals for detection via the counter-based sensor.

6. The medical drain system of claim 1, further comprising an automated valve coupled to the drain line, the automated valve configured to receive at least one wireless valve control signal to open or close the automated valve to regulate a flow of fluid through a portion of the drain line.

7. The medical drain system of claim 1, wherein the medical device transmits the at least one wireless signal to the remote liquid pump.

8. The medical system of claim 1, wherein the at least one fluid sensor transmits the at least one wireless signal to the remote pump.

9. The medical drain system of claim 1, wherein:

the at least one property is one or more of a flow rate or a flow volume, and the remote liquid pump is configured to operate to pump the fluid through the drain line to the drain when the one or more of the flow rate or the flow volume is above a threshold.

10. The medical system of claim 1, wherein the medical device is a gravity-based dialysis machine, and a distal end of the drain line is arranged at a greater height than a height of the valve of the gravity-based dialysis machine.

11. The medical drain system of claim 1, wherein the remote liquid pump is disposed remotely from the medical device by a distance of between three and one hundred feet.

* * * * *